(12) United States Patent
Altamirano

(10) Patent No.: US 8,398,544 B2
(45) Date of Patent: Mar. 19, 2013

(54) SURGICAL INSTRUMENT EQUIPMENT APPROPRIATE FOR MINI-INVASIVE SURGERY

(75) Inventor: José Daniel Altamirano, Concepción (AR)

(73) Assignee: Wom Industries SRL, Provincia de Tucuman (AR)

( * ) Notice: Subject to any disclaimer, the term of this patent is extended or adjusted under 35 U.S.C. 154(b) by 31 days.

(21) Appl. No.: 13/124,802

(22) PCT Filed: Oct. 13, 2009

(86) PCT No.: PCT/EC2009/000011
§ 371 (c)(1),
(2), (4) Date: Apr. 18, 2011

(87) PCT Pub. No.: WO2010/060436
PCT Pub. Date: Jun. 3, 2010

(65) Prior Publication Data
US 2011/0202081 A1    Aug. 18, 2011

(30) Foreign Application Priority Data
Oct. 20, 2008  (AR) .............................. P20080104571

(51) Int. Cl.
*A61B 1/00* (2006.01)
(52) U.S. Cl. ....................................................... 600/184
(58) Field of Classification Search ................. 600/184, 600/185, 186, 187, 201, 204, 205, 206, 208; 604/23, 164.01, 164.1, 164.11, 910
See application file for complete search history.

(56) References Cited

U.S. PATENT DOCUMENTS

| 6,488,620 | B1 * | 12/2002 | Segermark et al. | 600/208 |
| 7,753,901 | B2 * | 7/2010 | Piskun et al. | 604/539 |
| 7,850,600 | B1 * | 12/2010 | Piskun | 600/114 |

(Continued)

FOREIGN PATENT DOCUMENTS

| WO | 2006/019723 A2 | 2/2006 |
| WO | 2008/121294 A1 | 10/2008 |

(Continued)

OTHER PUBLICATIONS

International Search Report for PCT/EC2009/000011, dated Feb. 8, 2010.

*Primary Examiner* — Ryan Severson
*Assistant Examiner* — Jonathan W Miles
(74) *Attorney, Agent, or Firm* — Sughrue Mion, PLLC

(57) ABSTRACT

A surgical instrument equipment appropriate for mini-invasive surgery, inserted through natural orifices or incisions, made up by a device to have access to the patient's body, that is comprised by a rigid ring from which at least two extensions stem out in distal direction, which extensions act as separators and a multivalve flexible head which, when in use, is provided enveloping the external side of said rigid ring, and that comprises: at least one operative conducting duct for the access of at least one working instrument; a connector to insufflate and irrigate fluids; and a funnel to retain fluids that holds said multivalve flexible head that envelops the rigid ring, defining when assembled, a passage for said working instrument that is provided within at least a conducting duct and, in turn, is comprised by a clamp handle, a movement transmission element made by an external tubular sheath, a driving chuck and a clamp head is including an intrahead device.

14 Claims, 4 Drawing Sheets

U.S. PATENT DOCUMENTS

| | | |
|---|---|---|
| 8,137,266 B2 * | 3/2012 | Judson et al. .............. 600/184 |
| 8,137,267 B2 * | 3/2012 | Shelton et al. .............. 600/203 |
| 8,187,178 B2 * | 5/2012 | Bonadio et al. ............. 600/208 |
| 2002/0188275 A1 * | 12/2002 | McGuckin, Jr. ............. 604/506 |
| 2007/0049966 A1 * | 3/2007 | Bonadio et al. ............. 606/206 |
| 2007/0060939 A1 | 3/2007 | Lancial et al. |
| 2007/0225569 A1 * | 9/2007 | Ewers et al. ................ 600/206 |
| 2009/0036745 A1 * | 2/2009 | Bonadio et al. ............. 600/208 |
| 2009/0093752 A1 * | 4/2009 | Richard et al. .............. 604/24 |
| 2009/0177161 A1 * | 7/2009 | McGuckin et al. ...... 604/164.11 |
| 2009/0227843 A1 * | 9/2009 | Smith et al. ................ 600/208 |
| 2009/0270817 A1 * | 10/2009 | Moreno et al. .............. 604/264 |
| 2010/0081995 A1 * | 4/2010 | Widenhouse et al. ... 604/164.08 |
| 2010/0113886 A1 * | 5/2010 | Piskun et al. ............... 600/231 |
| 2010/0130825 A1 * | 5/2010 | Piskun ....................... 600/204 |
| 2010/0228092 A1 * | 9/2010 | Ortiz et al. ................. 600/204 |
| 2010/0268035 A1 * | 10/2010 | Oberlander et al. ......... 600/204 |
| 2011/0071359 A1 * | 3/2011 | Bonadio et al. ............. 600/184 |

FOREIGN PATENT DOCUMENTS

WO     2008/149332 A1     12/2008

* cited by examiner

SURGICAL INSTRUMENT EQUIPMENT APPROPRIATE FOR MINI-INVASIVE SURGERY

CROSS REFERENCE TO RELATED APPLICATIONS

This application is a National Stage of International Application No. PCT/EC2009/000011 filed Oct. 13, 2009, claiming priority based on Argentinean Patent Application No. 20080104571, filed Oct. 20, 2008, the contents of all of which are incorporated herein by reference in their entirety.

TITLE AND TECHNICAL FIELD OF THE INVENTION

The present invention relates to a surgical instrument equipment appropriate for mini-invasive surgery, inserted through natural orifices and/or incisions and supported by optical media.

STATE OF THE ART AND PROBLEMS TO SOLVE

At present, technological progress in surgery have led to what is known as minimally invasive surgery, a revolutionary technique by means of which operations are performed with viewing instruments and equipment passed into small incisions that allow reaching the surgical site without the need of major incisions.

The advantage of this technique is the trauma reduction of the healthy tissue, which leads to a lesser post-operative pain and a shorter post-operative is stay in hospital, maximizing costs. But minimally invasive surgery demands surgeons to learn more difficult surgical techniques.

The first major surgery to use laparoscopy was the cholecystectomy (removal of gall blabber) in 1985 and at present approximately 70% of said operations are performed by laparoscopic surgery.

It is also useful, in cases of doubt in diagnosis, to make a first approach by means of laparoscopy.

At present, in the prior art, laparoscopic and endoscopic surgical instruments are known.

In laparoscopic surgeries, multiple access ports or channels are used, with several incisions on the skin, one for each access device. In turn, each access port allows the entrance of one laparoscopic instrument at a time through only one operative channel.

In endoscopic surgery, the instrument in use, contrary to laparoscopic instruments due to their extreme flexibility, does not have an own directional axis but is adapted to the artificial or natural duct along which it moves.

The mentioned problem has led to conclude that its solution has to do with the provision of a "surgical instrument equipment appropriate for mini-invasive surgery" being able to solve the present limitations surgical instruments have and to circumscribe them by means of an access port where the surgeon and his assistances have access to and control, with precision, the movements of the technique to be used, at all possible angles of the surgical site, providing different possibilities of video-assisted diagnosis and treatment.

In the invention, this is attained by using:

Flexible and malleable semi-rigid devices and materials on working clamps that allow adopting a condition that memorizes the spatial positioning and repositioning (auto-locking) in different directions according to the angulations required by the task to be performed.

Different access devices which permit the simultaneous use of several working clamps through only one access port.

OBJECT OF THE INVENTION

The objective of the invention is to provide a surgical instrument equipment appropriate for mini-invasive surgery, used either through natural orifices or incisions, supported by optical media, which, through an access port and with any of the different access devices, can simultaneously insert and handle several working clamps or means having rigid and semi rigid features or both, which allow manoeuvrability and control of the practice to be conducted, at different planes and angulations as required by the medical technique.

Another objective of the present invention is to provide a surgical instrument equipment appropriate for mini-invasive surgery which access element to the surgical site can adopt different configurations and can remain in such a position.

Another objective of the present invention is to provide a surgical instrument equipment appropriate for mini-invasive surgery where the openings of the clamps (pliers, etc.) can rotate 360° whatever the configuration of the element to enter the surgical site may be.

Another objective of the present invention is to provide a surgical instrument equipment appropriate for mini-invasive surgery which access port can allow the entrance of working tools which have an operative head of greater diameter than the average transmission diameter of said tools, which can allow to combine the concept of minimal access with a surgical practice being safer than that of the laparoscopy, given the size of the operative tips of the tools.

DESCRIPTION OF FIGURES

The present invention will be better understood by means of the figures, in which.

DETAILED DESCRIPTION OF THE INVENTION

Figure 1:
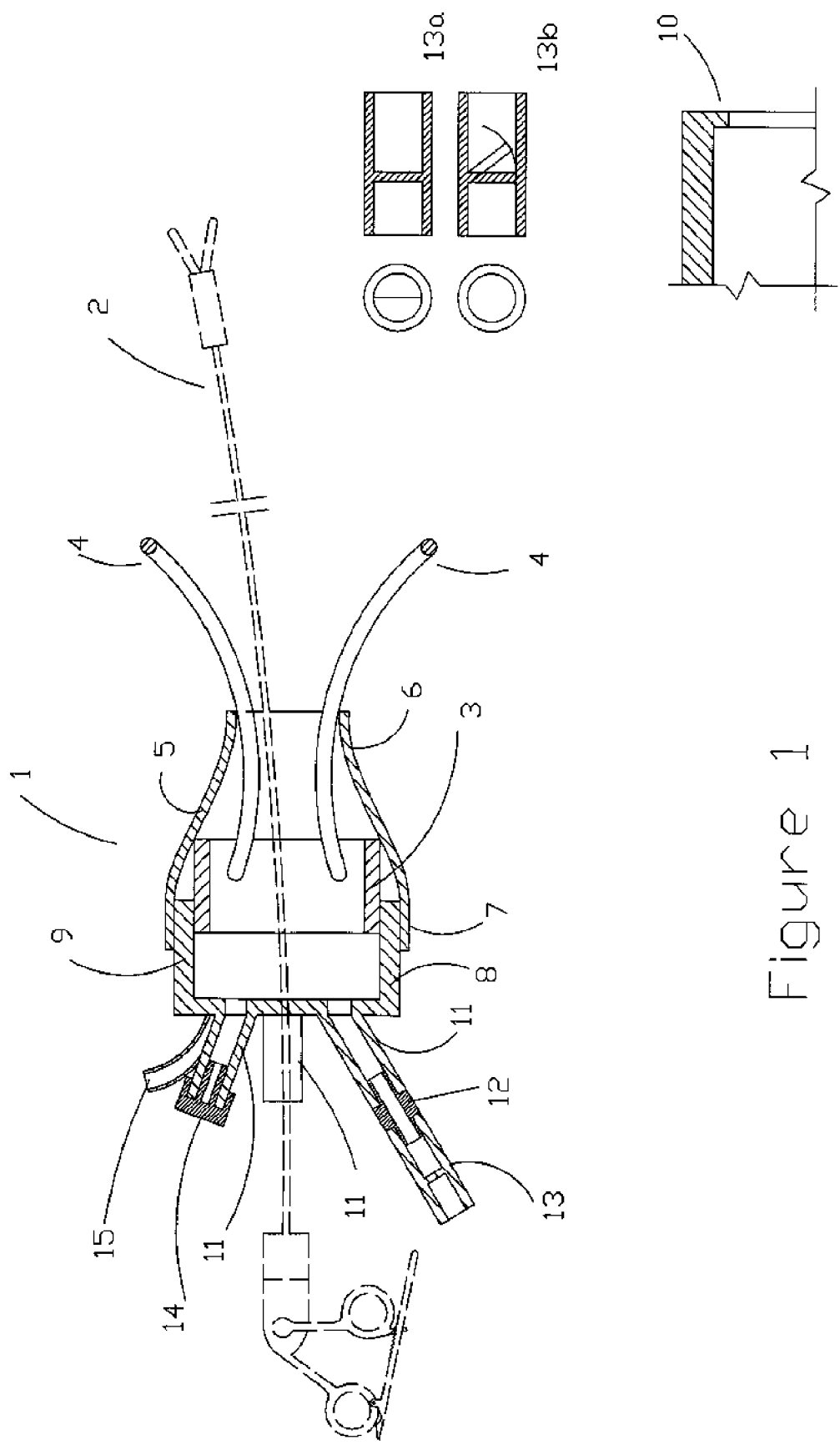
FIG. 1 shows the surgical instrument equipment comprised by the device, the working tool in operative position and two detailed views of the retaining valves and of the ledge of the multi-valve head.

FIG. 1 illustrates the surgical instrument equipment comprising a device (1) and a surgical tool (2) in operative position.

The device (1) is operatively provided at the access and comprises a is rigid ring (3) from which at least two extensions stem out in distal direction, which extensions act as separators (4) flexibly and preferably joined to the inner side of said rigid ring; said separators can be of different length and be slightly bent towards the outer side of the device; a flexible funnel (5) which will hold separators at the part where its diameter is smaller (6) and the rigid ring which will also be held by the funnel by at that part where its width is the largest (7); and a flexible multivalve head. This head has a cylindrical end (9) that will tightly fit onto the rigid ring and it also provides a ledge on its bottom to improve its attachment to the rigid ring. The material, either of the ring as well as of the separators, is preferably a material suitable for surgery, such as surgical steel, plastic or similar. While using these present instruments, the widest part of the funnel will fit at the outer side of the cylindrical end with flexible multi valve head causing a tight fastening which will allow to insufflate fluids into the patient's cavity or extract fluids from said cavity without loss of pressure. At the opposite end of the head, various access channels (11) are provided, four in the preferred embodiment, which are flexible to follow the angulations of the surgical instruments. These access channels are hollow extensions stemming out of the flexible multivalve head. To these access channels, valve connectors are coupled (12), the latter being cylindrical pieces with a circumferential butt of greater diameter, to which they are coupled to an access channel on one end and to the retaining valves (13), on the other. Retaining valves are cylindrical pieces having a valve medium for fluid retention inside. Reducers (14) are retaining valves of smaller diameter with their respective connectors also being of smaller diameter. Retaining valves and reducers avoid loss of pressure inside the patient's cavity and allow the insertion of working elements for the surgery. Retaining valves are preferably diaphragm-type (13a) or hing-type valves (13b). The flexible multi valve head provides, on the channels' side, an additional is connecting duct (15) to insufflate or irrigate fluids into the patient's cavity.

Figure 2:
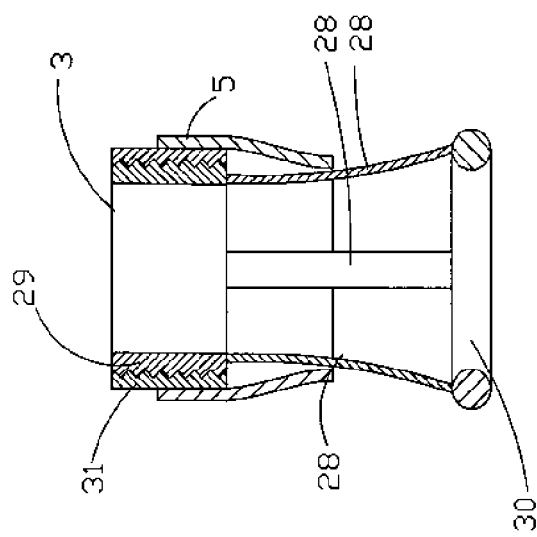
FIG. 2 shows the device in a first embodiment comprising a pair of threaded joined concentric rigid rings.

In FIG. 2, a first embodiment of the invention is shown, wherein the rigid ring is made up by two concentric pieces (16; 17), both joined to each other by means of a thread (18). The external piece (17) shows an inner thread and has a first separator (19) firmly fixed to its external surface and it is the piece that holds the flexible multivalve head when in use. The inner piece (16) shows an external thread and has a second separator (20) firmly fixed to its inner surface. When using surgical instruments, both separators are coincidentally located on a same radius and the flexible funnel (5) is mounted on both separators (this embodiment is illustrated in FIG. 2 with dotted lines). When both concentric pieces are rotated, separators get apart up to a desired position, preferably one diametrically opposed to the other, and the flexible funnel acquires the new shape adopted by said separators in their new position: the steady separator (19) and the new position of the second separator (20) (this embodiment is illustrated in FIG. 2 in position (21)). Now, in this embodiment, it is possible to assemble the flexible multivalve head on the external concentric piece and subsequently the flexible funnel on said flexible multivalve head.

Figure 3:
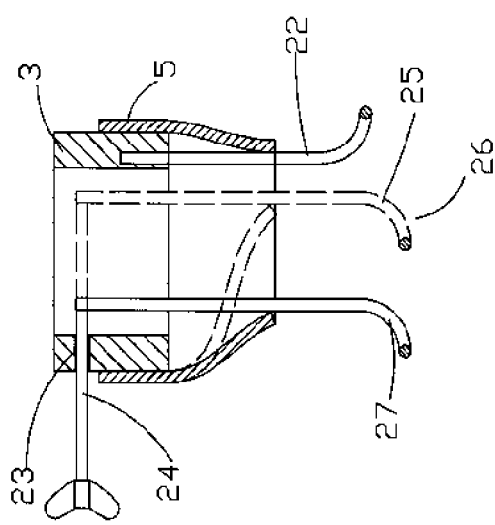
FIG. 3 shows the device in a second embodiment wherein a movable separator is driven by a shifting screw.

In FIG. 3, a second embodiment of the invention is seen, wherein the rigid ring (3) shows a steady separator (22) on its inner side and, on the opposite side of said steady separator, a threaded hole (23) is provided, within which a screw (24) rotates. The inner end of said screw is joined to a movable separator (25) and in its external end an element known in the art is provided to tighten/release said screw. The displacement the screw performs with respect to the rigid ring radially moves the movable separator. To use this embodiment, both separators are closely placed (initial layout (26) of movable separator illustrated in FIG. 3 with dotted line), the flexible funnel (5) is placed on said separators and the rigid ring and subsequently the movable separator is displaced by means of the screw. The funnel will follow the movable separator up to its operative position (27).

In all these embodiments, separators are made of a thin element, elongated in "U" shape, whether rigid, flexible or a combination of both, where all of its sides are blunt and its curves are soft. Its distal ends can be bent toward the inner part of the device.

Tests carried out by the applicant himself have shown that a slight angulation outwards at the proximal side of the separators improves the fastening and reduces leaks of fluids on the outer side of the device.

Next, several embodiments of the invention are described, wherein the opening of the access is made by means of a combination of at least an elastic ring with longitudinal devices attached to it by one of its ends, with a rigid ring that forces these longitudinal devices to get separated one from the other, forcing the opening of the patient's cavity.

Figure 4:
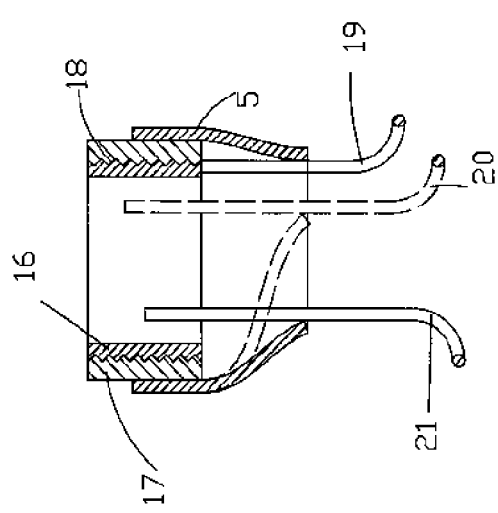
FIG. 4 shows the device in a third embodiment wherein a flexible ring is provided with a set of straps or ropes.

In FIG. 4, a third embodiment of the invention is shown, wherein separators are retracting straps or ropes (28), preferably of elastic material, joined on one end to a rigid head holder ring (29) and on the other to an elastic ring (30) which shape can be modified (get deformed.). A retracting rigid ring (31) provides an external thread in which the rigid head holder ring fits, both working in conjunction. By using this embodiment, the modified (deformed) elastic ring is inserted with the straps together with the funnel (5) by the wall of the patient's cavity; once this set is inserted, the flexible ring goes back to its original shape and both rigid rings get locked, the retractring and the head holder rings. By rotating the retracting ring, the rigid head holder ring is moved away from the patient, dragging the flexible ring against the patient's opening and against the retracting ring, the straps get tight and rigidly enough so as to bear the pressure of entering the patient's cavity through the flexible funnel.

Figure 5:
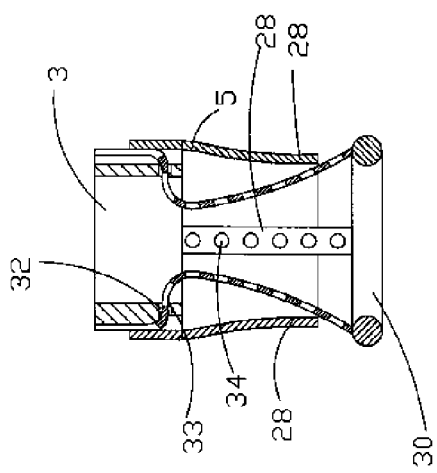
FIG. 5 shows the device in a fourth embodiment wherein a flexible ring is provided with a set of straps or ropes that fastens by means of bolts on the rigid ring.

In FIG. 5, a fourth embodiment of the invention is shown, wherein an elastic ring (30) is seen at the distal end of the retracting straps (28) to which it is firmly attached. Radial slots (32) are made on the rigid ring (3), which slots is have a bolt (33) at their entrance. The retracting straps are of flexible material, with holes (34) to fasten to said bolts. By pulling the straps toward the rigid ring and fastening the bolt onto the hole, the flexible ring is dragged and fixed near said rigid ring; at this moment, the straps get tight and rigidly enough to exert pressure on the flexible funnel and on the access to the patient's cavity.

Figure 6:
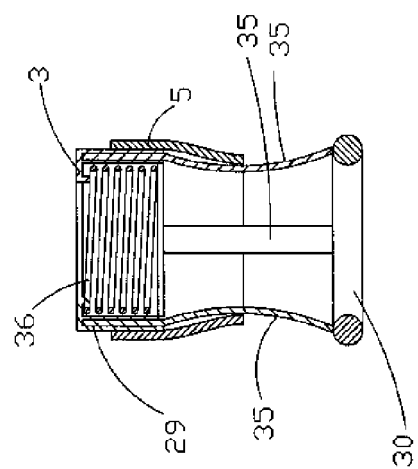
FIG. 6 shows the device in a fifth embodiment wherein a spring is provided, where said spring pulls from the flexible ring and the set of straps or ropes to the rigid ring.

In FIG. 6, a fifth embodiment of the invention is illustrated, wherein a flexible ring (30) is provided with an end of the non flexible straps (35) fixed to said ring and the opposite end, to the upper edge of a spring (36) which will fit into the rigid ring (3). A set is made with the spring being compressed and when stretching said spring, this is recovered by dragging on the straps that push the flexible ring against the rigid ring; at this moment, said straps get tight and rigidly enough to exert pressure on the flexible funnel and on the access opening of the patient.

Figure 7:
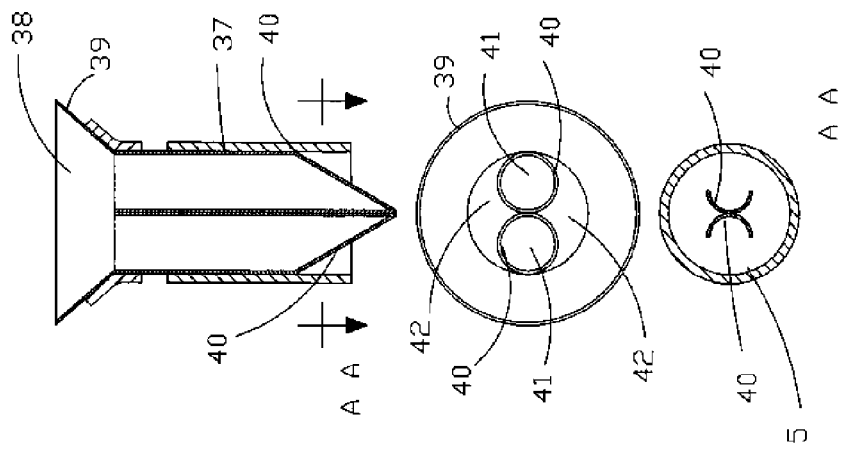
FIG. 7 shows the device in a sixth embodiment consisting of a sheath.

In FIG. 7, a sixth embodiment is observed, consisting of an external sheath (37) that can have divisions of the inner access channel of the rigid ring (3). This external sheath comprises at least one channel of internal access (38) fixed to a conical retaining ring (39), so that it tightly fits into a rigid ring (not shown). Fastened to the bottom, two furrows (40) are provided, being abutted one to the other, preferably by welding, which create 4 passages, two inner ones to each furrow (41) and two external ones (42), between the furrows and the external sheath. The furrows conform the inner sheath. These four passages, being independent at the initial stage, facilitate the arrangement of surgical tools. Distal ends of the tubes can be bevelled. An apron (43) made of flexible material is present, which provides impermeability and tightness to the rigid ring. As well, another quantity of internal access channels can be provided. When used, a flexible funnel is mounted on the external sheath to avoid leak of fluids.

Figure 8:
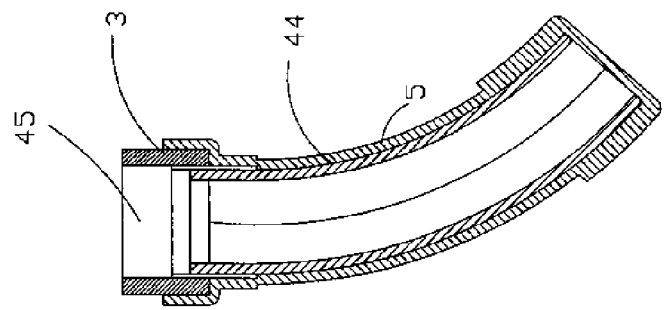
FIG. 8 shows the device in a seventh embodiment comprising a dilating device.

FIG. 8 shows a seventh embodiment which comprises a dilating device that consists of a semi-rigid tubular structure (44) with at least one channel (45) inside. The semi-rigid tubular structure can be made up by a tube itself or by at least a pair of separators, which are substantially longer than wider, having a soft curve along its flat sides. At one end, a rigid ring (3) is provided and at the opposite end, a surface with soft blunt edges is seen. If assembled by means of separators, impermeability is attained by mounting a flexible funnel on said separators.

Figure 9:
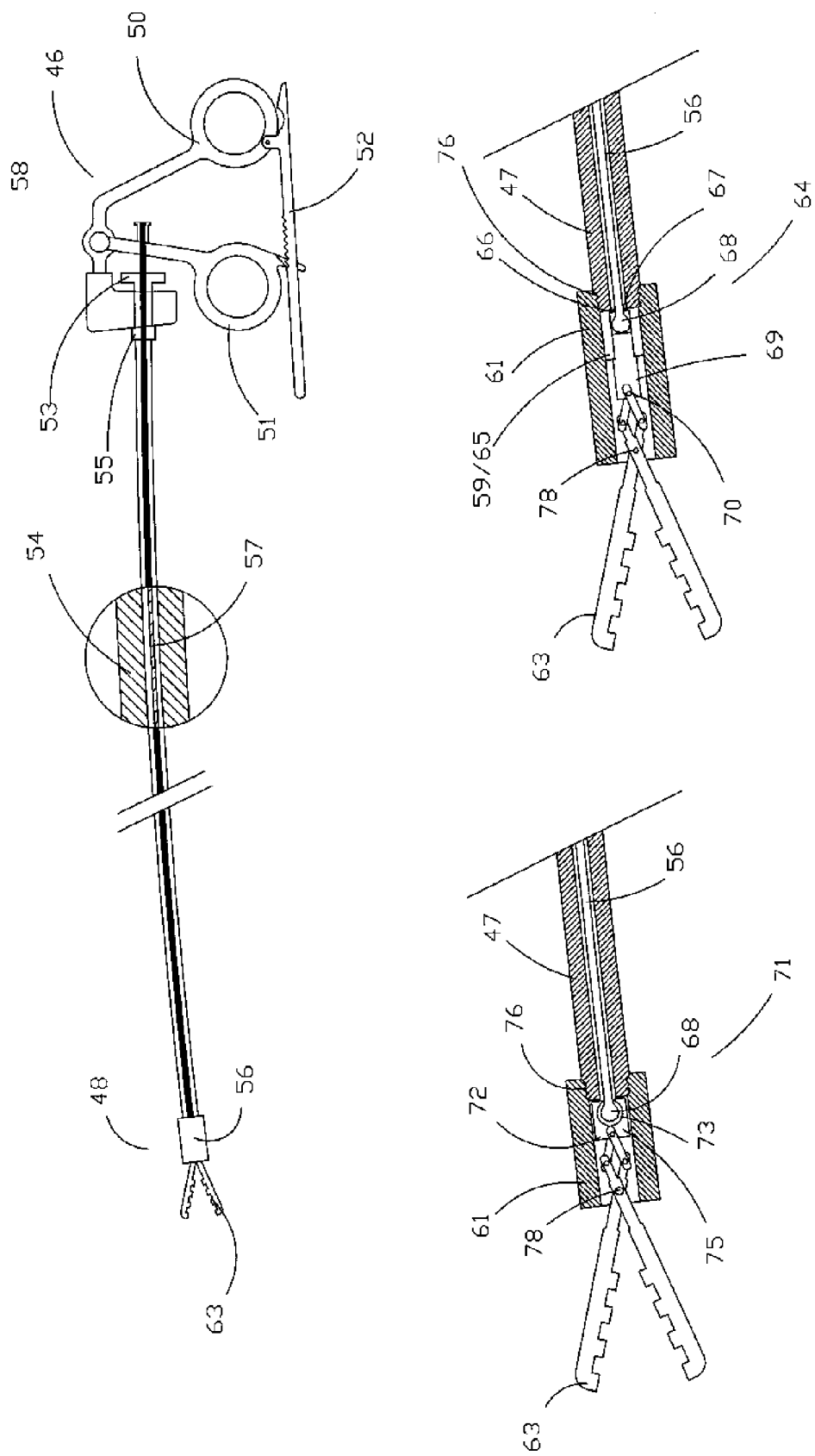
FIG. 9 shows the working tools and details of the intrahead devices.

The surgical tool (2) to be used with the surgical instrument equipment appropriate for mini-invasive surgery comprises a clamp handle (46), a movement transmission element (47) and a clamp opening (48). This is seen in FIG. 9.

The clamp handle consists of a pair of articulated arms (49) ergonomically adapted to the operator's hand, where one arm is steady (50) and the other is movable (51). They can be provided with a zipper system (52) to lock the closure of the operative opening. Jointly to the steady arm, a wrench (53) is provided to rotate the tubular sheath. The steady arm can be provided with a cautery connector (not shown).

The element that transmits the movement consists of a tubular sheath (54) with rotatory movement, with its proximal element (55) fastened to the steady arm of the clamp handle and, at the opposite distal end, an operative tool head (56). Inside the tubular sheath, a driving chuck (57) is provided, which comprises a thin and elongated element with a proximal fastening (58) to the movable arm which does not allow its rotation but it does permit its longitudinal shifting and, at the opposite distal end, with a fastening to the intrahead device (59).

The driving chuck is a malleable, cylindrical, elongated piece (60) having at least a semi-rigid section, preferably one of the ends. One end, the proximal one, is linked to the movable arm of the clamp handle with a joint that does not allow its rotation but it allows a longitudinal shifting activated by said movable arm. The distal end finishes with a ball that longitudinally displaces the piece to which it is joined and allows its rotation. The fact of being malleable allows its shape to be changed (to be deformed) maintaining its new position. The different configurations this driving chuck can adopt allow the free rotation of the tubular sheath which covers it, and of the clamp opening fixed to the sheath.

The tubular sheath is preferably flexible, cylindrical and elongated, within which the driving chuck is lodged. The relation between both, as from specially provided joints, is that the tubular sheath allows the longitudinal displacement of the driving chuck along its interior, while this does not hinder the tubular sheath to fully rotate on its axis. This movement combination is achieved by operating the wrench of the clamp handle that drags the tubular sheath and this drags the clamp head. The tubular sheath fully covers the driving chuck and can have an electric insulation.

The importance of the present invention is that the tubular sheath can be narrower and thinner than the head and than the operative tool. This means that, through an only access port, several operative tools can be inserted, without any interference among them.

The clamp head (61) is a rigid and tubular device which proximal end tightly couples (by means of a thread) with the distal end of the tubular sheath. The clamp head can receive the 360° rotation of the tubular sheath transmitting same, in turn, to the intrahead device (62) but it does not transmit said rotating movement to the driving chuck. The intrahead device is located inside the clamp head and is responsible for the proper longitudinal movement in both ways transmitted by the driving chuck as from the movement of the clamp handle, and of the rotating movement of the tubular sheath to the clamp mouth (63).

The present patent application comprises two different models of intrahead devices. In the first model (64) a cylinder (65) is provided with a lid (66) on the proximal side that has a central hole (67) having a diameter slightly larger than that of the wire of the driving chuck. The driving chuck ends in a ball (68) having a larger diameter than all the length of the driving chuck and a larger diameter than the central hole of the lid of the driving chuck, where it is abutted when the driving chuck is threaded within the central hole. The ball inside the intrahead device is locked with a plug (69), allowing its relative rotation. This plug is longer than the cylinder and provides, at the distal side, a hole (70) transversally centered where the articulations to operate the tools are coupled to a bolt. In the second model (71) of the intrahead device, a round mass (72) is provided where, at the proximal end, a slot followed by a spherical cavity (73) is provided, where the spherical distal end of the driving chuck is lodged, allowing its relative rotation. The distal end of the intrahead device finishes in a flat configuration with a hole (75) transversally centered where the bolt of the operative articulation of the clamp mouths is fixed.

In the present invention, the location of these intrahead devices that allow the rotation and longitudinal displacement, is the novelty.

The clamp head is a device within which the intrahead device is displaced with an inner thread (76) where the tubular sheath is coupled. At the opposite end, a central, "U" shaped arm is provided, with two holes (77) on both arms, where a bolt is inserted to fix the head to the clamp mouth.

Clamp tips are 'per se' the working elements within the patient's cavity. They allow the dissection, pressing, cutting, cauterization, etc. as required by the surgical operation. These tips are provided with articulations that transform the linear movement of the driving chuck into closing and opening of the clamp tips when working against the inner conical surface of the intrahead device.

Having described and defined the nature of the invention as well as the manner in which same can be put into practice based on its main objective, the following is claimed as invention and of exclusive ownership:

1. A surgical instrument equipment appropriate for mini-invasive surgery, used through natural orifices or incisions, characterized in that it comprises a device to enter the patient's body (1) which includes a rigid ring (3) provided outside of the patient's body, from which at least two extensions (4) stem out in distal direction, which extensions act as separators, and a multivalve flexible head (8) that, in use, it is provided enveloping the external side of said rigid ring, and that comprises at least an operative channel (11) to insert at least one working tool (2), a connector to insufflate and irrigate fluids (15); and a funnel to retain fluids (5) which holds said multivalve flexible head that envelops the rigid ring; said funnel defines, when assembled, a passage for the mentioned operative tool which is flexible, semi rigid and that is provided inside at least one conducting duct, and, in turn, comprises a clamp handle (46), a movement transmission element made up by an external tubular sheath (54) that is fully flexible, a malleable and semi rigid driving chuck (57) and a clamp head (48) which includes an intrahead device (59) that allows the opening of the working tool and that the head can make a 360° turn without changing the position given by the driving chuck.

2. A surgical instrument equipment according to claim 1, characterized in that said multivalve flexible head comprises a cylindrical end (9) that can be coupled on said rigid ring, and it can further have an inner ledge on its bottom; and an opposite end at which at least one flexible access channel is provided, which emerges out of the multivalve flexible head, to which a valve connector (12) is connected, being this a tubular piece with two different external diameters, where the distal end has less diameter and that which is inserted into an access channel and to the retaining valves (13) has a larger outer diameter; the retaining valves are fully flexible tubular pieces having a medium to retain fluids inside; and further provides an accessory (additional) channel -independent from the access channels- to insufflate and irrigate fluids to the patient's cavity.

3. A surgical instrument equipment according to claim 1, characterized in that the rigid ring comprises two concentric pieces (17) each one joined to the other by means of a thread (18), where the external piece includes a first separator (19) on its external side; and the inner piece includes a second separator (21) on its inner side, and the relative movement of both pieces has got at least two positions: a first position with both separators placed on the same radius (19, 20) and the second position, with both separators placed on the same diameter (19, 21).

4. A surgical instrument equipment according to claim 1, characterized in that the rigid ring has got a steady separator (22) in its interior and opposite to said separator, a threaded hole (23) is provided, within which a screw (24) is turned; at the inner end of this screw, a movable separator (26) is joined and at the opposite end, an element to fasten/unscrew said screw is provided.

5. A surgical instrument equipment according to claim 1, characterized in that the rigid ring supports at least two extensions that act as separators and basically have a "U" shape, where all edges are blunt, curves soft and their distal ends are bent toward the outer side of the surgical instrument equipment.

6. A surgical instrument equipment according to claim 1, characterized in that the rigid ring allows, on its inner side, a tight fitting of a spring and further comprises at least two non flexible straps (35) joined to an elastic ring (30) by their distal ends and to the upper edge of said spring by their proximal ends, where the spring is mounted within the rigid ring being fitted therein, and dragging the elastic ring against the rigid ring.

7. A surgical instrument equipment according to claim 1, characterized in that it comprises an external sheath (37) with a rigid ring on one end and one free end with soft curves and blunt edges, providing an internal access channel.

8. A surgical instrument equipment according to claim 7, characterized in that said internal access channel preferably is four access channels (41, 42) by providing furrows (40) joined by their directrix within the external sheath; the distal ends of said furrows can be bevelled.

9. A surgical instrument equipment according to claim 1, characterized in that it comprises a rigid ring joined to a semi rigid tubular structure (44) that forms an access channel.

10. A surgical instrument equipment according to claim 9, characterized in that said semi rigid tubular structure is made up by a pair of separators substantially longer than wider and with soft curves on their flat sides.

11. A surgical instrument equipment according to claim 1, characterized in that said driving chuck (57) is made of a thin and elongated wire-like element, so that it can adopt and memorize different positions, that it provides at its proximal end two depressions diametrically opposed and at its distal end, a ball of larger diameter than that of the thin and elongated element of the driving chuck.

12. A surgical instrument equipment according to claim 1, characterized in that said intrahead device (64) comprises a cylindrical body (65) where at its proximal end the ball (68) of the driving chuck is lodged, which ball pushes while displacing said intrahead device, moving it along the interior of the tool head (61) and transmits the resulting force to the articulations and further, said intrahead device allows a 360° rotation of the tool head when same receives the rotation originated in the wrench and transmitted by the tubular sheath.

13. A surgical instrument equipment according to claim 1, characterized in that said intrahead device comprises a cylinder with a lid on its proximal side that provides a central hole slightly larger than the diameter of the driving chuck, which ball abuts when the chuck gets threaded within the former; finally, the intrahead device provides a plug, longer than the cylinder and has, on the distal side, a hole transversally centered, which hole is provided so that the articulations can couple, and said plug places the ball within the intrahead device, allowing its relative rotation.

14. A surgical instrument equipment according to claim 1, characterized in that said intrahead device (71) comprises a round mass (72) where at the proximal end a slot followed by an spherical cavity is provided, where the spherical distal end of the driving chuck is lodged, allowing its relative rotation; the distal end of said intrahead device finishes in a flat configuration with a hole transversally centered (75) where the bolt of the moving articulation of the clamp tips is fixed.

\* \* \* \* \*